United States Patent [19]

Maschler et al.

[11] Patent Number: 5,321,029

[45] Date of Patent: Jun. 14, 1994

[54] XANTHINES

[75] Inventors: Harald Maschler; Rolf T. Wilke; Johannes Jukna, all of Gronau, Fed. Rep. of Germany

[73] Assignee: Beecham-Wuelfing GmbH & Co.K.G., Fed. Rep. of Germany

[21] Appl. No.: 821,333

[22] Filed: Jan. 13, 1992

Related U.S. Application Data

[63] Continuation of Ser. No. 634,978, Jan. 7, 1991, abandoned, which is a continuation of Ser. No. 436,233, Nov. 14, 1989, abandoned.

[30] Foreign Application Priority Data

Nov. 14, 1988 [GB] United Kingdom ............... 88265954

[51] Int. Cl.$^5$ ..................... A61K 31/52; C07D 473/06
[52] U.S. Cl. .................... 514/263; 514/265; 544/267; 544/271; 544/273
[58] Field of Search ............... 514/263, 265; 544/267, 544/271, 273

[56] References Cited

U.S. PATENT DOCUMENTS

| | | | |
|---|---|---|---|
| 2,602,795 | 7/1952 | Papesch et al. | 544/311 |
| 4,089,959 | 5/1978 | Diamond | 514/263 |
| 4,233,303 | 11/1980 | Bergstrand et al. | 514/263 |
| 4,644,001 | 2/1987 | Kjellin et al. | 514/263 |
| 4,657,910 | 4/1987 | Morgan | 514/263 |
| 4,883,801 | 11/1989 | Nathanson | 514/263 |

FOREIGN PATENT DOCUMENTS

| | | |
|---|---|---|
| 0001735 | 5/1979 | European Pat. Off. . |
| 0010531 | 4/1980 | European Pat. Off. . |
| 2340318 | 9/1977 | France . |
| 2346353 | 10/1977 | France . |
| 0136281 | 10/1980 | Japan ................... 544/271 |
| 1441562 | 7/1976 | United Kingdom . |

*Primary Examiner*—Mark L. Berch
*Attorney, Agent, or Firm*—Roseman & Colin

[57] ABSTRACT

A compound of formula (I):

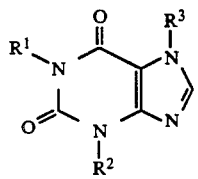

or where appropriate a pharmaceutically acceptable salt thereof, wherein $R^1$ and $R^2$ each independently represent a moiety of formula (a):

$$-(CH_2)_m-A \qquad (a)$$

wherein m represents zero or an integer 1, 2 or 3, A represents a substituted or unsubstituted cyclic hydrocarbon radical; and $R^3$ represents hydrogen, substituted or unsubstituted alkyl, substituted or unsubstituted alkenyl, substituted or unsubstituted alkynyl or a moiety of formula (a) as defined above; a pharmaceutical composition comprising such a compound a process for preparing such a compound and the use of said compound and said composition in medicine.

12 Claims, No Drawings

XANTHINES

This is a continuation of application Ser. No. 07/634,978, filed Jan. 7, 1991, abandoned, which is a continuation of application Ser. No. 07/436,233 filed Nov. 14, 1989, abandoned.

This invention relates to compounds having pharmacological activity, to pharmaceutical compositions containing such compounds, to a process for the preparation of such compounds, and to the use of such compounds and compositions in medicine.

European Patent Application, Publication Number 0,010,531 discloses certain 3-alkylxanthines which are described as beng useful for the treatment of obstructive airways disease and cardiac disease.

Japanese Kokai 55/136281 discloses certain 1-(cyclopropylmethyl)-3,7-dimethylxanthines having useful pharmacological properties.

United Kingdom Patent Number 1,441,562 discloses certain 7-(oxoalkyl)-1,3,-dialkyl xanthines which are described as being effective in increasing the blood flow through skeletal muscle. GB 1,441,562 also discloses certain 1,3-dialkyl xanthines which are described solely as intermediates.

It has now been discovered that certain xanthines, some of which fall within the scope of the general formulae of the xanthines disclosed in GB-1,441,562 but which are not specifically disclosed therein, have especially useful pharmacological properties and in particular show good metabolic stability.

The compounds of the present invention are active in increasing the oxygen tension in ischaemic skeletal muscle. This property results in an increase in the nutritional blood flow through ischaemic skeletal muscle which in turn indicates that the compounds of the invention are of potential use as agents for the treatment of peripheral vascular disease such as intermittent claudication.

The compounds of the present invention also have a protective effect against the consequences of cerebral metabolic inhibition. The compounds of the present invention also improve data acquisition or retrieval following transient forebrain ischaemia. The compounds are therefore useful in the treatment of cerebral vascular disorders and neuronal degenerative disorders associated with learning, memory and cognitive dysfunctions including cerebral senility, multi-infarct dementia and senile dementia of the Alzheimer type.

The compounds of the invention are also indicated to have neuroprotectant activity. They are therefore useful in the prophylaxis of disorders associated with neuronal degeneration resulting from ischaemic events, including cerebral ischaemia due to cardiac arrest, stroke and also after cerebral ischaemic events such as those resulting from surgery and/or during childbirth. In addition treatment with the compound is indicated to be of benefit for the treatment of functional disorders resulting from disturbed brain function following ischaemia.

The compounds of the present invention also act as phosphodiesterase inhibitors and elevate cyclic AMP levels and are therefore of potential use in the treatment of proliferative skin disease in human or non-human mammals.

The compounds of the invention are also indicated to have bronchodilator activity and thus to be of potential use in the treatment of disorders of the respiratory tract, such as reversible airways obstruction and asthma.

Accordingly in a first aspect, the invention provides a compound of formula (I):

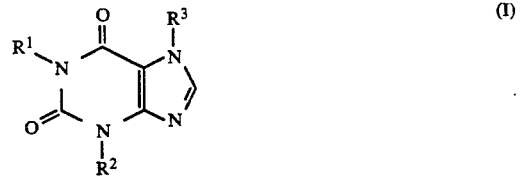

or where appropriate a pharmaceutically acceptable salt thereof, wherein $R^1$ and $R^2$ each independently represent a moiety of formula (a):

$$—(CH_2)_m—A \qquad (a)$$

wherein m represents zero or an integer 1, 2 or 3, A represents a substituted or unsubstituted cyclic hydrocarbon radical; and $R^3$ represents hydrogen, substituted or unsubstituted alkyl, substituted or unsubstituted alkenyl, substituted or unsubstituted alkynyl or a moiety of formula (a) as defined above.

There is a sub group of the compounds of formula (I) or where appropriate a pharmaceutically acceptable salt thereof, wherein $R^1$ and $R^2$ both represent cyclohexyl and $R^3$ represents substituted or unsubstituted alkyl, substituted or unsubstituted alkenyl, substituted or unsubstituted alkynyl or a moiety of formula (a) as defined above.

There is a sub-group of the compounds of formula (I), or where appropriate a pharmaceutically acceptable salt thereof, wherein $R^1$ and $R^2$ each independently represent a moiety of formula (a):

$$—(CH_2)_m—A \qquad (a)$$

wherein m represents zero or an integer 1, 2 or 3, A represents a substituted or unsubstituted cyclic hydrocarbon radical; and $R^3$ represents hydrogen, substituted or unsubstituted $C_{1-6}$ alkyl, substituted or unsubstituted $C_{2-6}$ alkenyl, substituted or unsubstituted $C_{2-6}$ alkynyl or a moiety of formula (a) as defined above.

In the abovementioned formula (I), the values of $R^1$ and $R^2$ may be the same or different, however, it is more favoured if the values of $R^1$ and $R^2$ are the same.

One sub-group of the compounds of formula (I) are those wherein $R^1$ and $R^2$ each independently represents a moiety of formula (a), wherein m represents zero and $R^3$ represents substituted or unsubstituted alkyl, especially $C_{1-6}$ alkyl, substituted or unsubstituted alkenyl, especially $C_{2-6}$ alkenyl, substituted or unsubstituted alkynyl, especially $C_{2-6}$ alkynyl, or a moiety of formula (a) as defined in relation to $R^3$ in formula (I).

One sub-group of the compounds of formula (I) are those wherein $R^1$ and $R^2$ each independently represents a moiety of formula (a), wherein m represents an integer 1, 2 or 3 and $R^3$ represents hydrogen, substituted or unsubstituted alkyl, especially $C_{1-6}$ alkyl, substituted or unsubstituted alkenyl, especially $C_{2-6}$ alkenyl, substituted or unsubstituted alkynyl, especially $C_{2-6}$ alkynyl, or a moiety of formula (a) as defined in relation to $R^3$ in formula (I).

Suitably, A represents a substituted or unsubstituted $C_{3-8}$ cycloalkyl group, especially a $C_{3-6}$ cycloalkyl group, such as a $C_{3-5}$ cycloalkyl group or a $C_{3-4}$ cycloalkyl group.

In particular, A represents a substituted or, especially, an unsubstituted cyclopropyl, cyclobutyl or cyclopentyl group, or a cyclohexyl group.

Hence, in a further particular aspect, A represents an unsubstituted cyclic hydrocarbon radical, such as an unsubstituted $C_{3-8}$ cycloalkyl group, especially an unsubstituted $C_{3-6}$ cycloalkyl group, for example an unsubstituted $C_{3-5}$ cycloalkyl group or an unsubstituted $C_{3-4}$ cycloalkyl group.

Favourably, A represents an unsubstituted cyclobutyl group.

Preferably, A represents an unsubstituted cyclopropyl group.

Thus in a most preferred aspect of the invention, $R^1$ and $R^2$ both represent cyclopropylmethyl.

Suitably, m represents zero or the integer 1.

Favourably, m represents zero.

Preferably, m represents 1.

Suitably, $R^3$ represents hydrogen.

When $R^3$ represents an alkyl group it is preferably a substituted alkyl group.

When $R^3$ represents a moiety of formula (a) it is suitably a moiety (a) wherein A is $C_{3-8}$ cycloalkyl, for example cyclopropylmethyl; and wherein m is suitably 1.

Suitably, $R^3$ represents substituted or, less favourably, unsubstituted $C_{1-6}$ alkyl.

Favoured alkyl groups for $R^3$ include an n-propyl, n-butyl or n-hexyl group, especially an n-propyl group.

Suitable optional substituents for any alkyl, alkenyl or alkynyl group, and especially for any alkyl group, includes up to three substituents, but preferably one substituent, selected from: oxo or a pharmaceutically acceptable acetal or ketal thereof, hydroxy or a pharmaceutically acceptable ester thereof, halogen and nitrile, especially oxo and hydroxy.

A preferred optional substituent for any alkyl group being that wherein the substituent is present on the penultimate carbon atom of the alkyl group, for example on the 2-carbon atom of an n-propyl group or on the 5-carbon atom of an n-hexyl group.

Particular substituted alkyl groups include 2-oxo- or -2-hydroxy n-propyl groups, 3-oxo or 3-hydroxy n-butyl groups or 5-oxo or 5-hydroxy n-hexyl groups, or the said acetal or ketal derivatives of said oxo groups or the said ester derivatives of said hydroxy groups.

When m represents zero, favoured examples of the variable $R^3$ include 2-oxopropyl and 2-hydroxypropyl.

When m represents an integer 1, 2 or 3, favoured examples of the variable $R^3$ include hydrogen, 2-oxopropyl and 2-hydroxypropyl.

Most preferably $R^3$ represents a 2-oxopropyl group.

The compounds of formula (I) wherein $R^3$ represents hydrogen, may form pharmaceutically acceptable salts. Suitable pharmaceutically acceptable salts are pharmaceutically acceptable base salts including metal salts, such as alkali metal salts for example sodium salts, or organic amine salts such as that provided with ethylenediamine.

The pharmaceutically acceptable salts are prepared using conventional procedures.

When used herein the term 'cyclic hydrocarbon radical' includes single ring and fused ring, cyclic hydrocarbons comprising up to 8 carbon atoms in each ring, suitably up to 6 carbon atoms, favourably up to 5 carbon atoms, for example 3, 4 or 5 carbon atoms, or 6 carbon atoms.

Suitable optional substituents for any cyclic hydrocarbon radical includes an alkyl group or a halogen atom.

In a favoured form the cyclic hydrocarbon radical is unsubstituted.

When used herein the term 'alkyl' includes straight and branched chain alkyl groups, containing from 1 to 12 carbon atoms, suitably from 1 to 6 carbon atoms for example 1, 2, 3 or 4 carbon atoms.

When used herein the term 'alkenyl' includes straight and branched chain alkenyl groups containing from 2 to 12 carbon atoms, suitably from 2 to 6 carbon atoms, for example 2, 3 or 4 carbon atoms.

When used herein the term 'alkynyl' includes straight and branched chain alkynyl groups containing from 2 to 12 carbon atoms, suitably from 2 to 6 carbon atoms, for example 2, 3 or 4 carbon atoms.

Suitable acetal derivatives of any oxo group include pharmaceutically acceptable acetal derivatives including for example those acetals provided by $C_{1-6}$ alkanols especially those provided by ethanol.

Suitable keto derivatives of any oxo include pharmaceutically acceptable acetal groups including for example those provided by 1,2-dihydroxyethane or 1,3-dihydroxypropane.

Suitable ester derivatives of any hydroxy group include pharmaceutically acceptable esters including for example those provided by $C_{1-6}$ carboxylic acids.

Certain of the compounds of formula (I) or formula (I') can exist in more than one stereoisomeric form, the invention extends to each of these forms whether as single isomers or as mixtures thereof.

When used herein the expression 'proliferative skin diseases' means benign and malignant proliferative skin diseases which are characterized by accelerated cell division in the epidermis, dermis or appendages thereto, associated with incomplete tissue differentiation. Such diseases include: psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant keratosis, ache, and seborrheic dermatitis in humans and atopic dermatitis and mange in domesticated animals.

The compounds of the invention are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%.

The invention further provides a process for the preparation of a compound of formula (I), wherein $R^3$ represents substituted or unsubstituted alkyl, substituted or unsubstituted alkenyl, substituted or unsubstituted alkynyl or a moiety of formula (a) as defined above in relation to formula (I), which process comprises reacting a compound of formula (II):

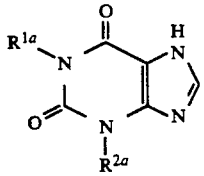

wherein $R^{1a}$ represents $R^1$, as defined in relation to formula (I), or a group convertible to $R^1$ and $R^{2a}$ represents $R^2$, as defined in relation to formula (I), or a group convertible thereto, with a compound of formula (III):

$$R^{3a}-X \qquad (III)$$

wherein $R^{3a}$ represents $R^3$, as defined above in relation to this process, or a group convertible thereto and X represents a leaving group; and thereafter, if required, carrying out one or more of the following optional steps:

(i) converting any group $R^{1a}$ to $R^1$ and/or $R^{2a}$ to $R^2$;
(ii) converting $R^{3a}$ to $R^3$;
(iii) converting a compound of formula (I) into a further compound of formula (I); and
(iv) forming a pharmaceutically acceptable salt thereof.

Suitably, X represents a halogen atom, preferably a chlorine atom.

The reaction between the compounds of formulae (II) and (III) may be carried out under any suitable conventional conditions, for example when X represents a halogen atom, the reaction may conveniently be carried out in the presence of a base such as an alkali metal alkoxide, for example sodium ethoxide, or an organic base, for example triethylamine, conveniently in a solvent such as toluene, at any temperature providing a suitable rate of formation of the compound of formula (I), for example at an elevated temperature such as a temperature in the range of from 60° C. to 130° C.

The present invention also provides a process for preparing a compound of formula (I) or where appropriate a pharmaceutically acceptable salt thereof, by the dehydrating cyclisation of a compound of formula (IV):

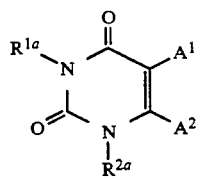

wherein $R^{1a}$ represents $R^1$, as defined in relation to formula (I), or a group convertible to $R^1$ and $R^{2a}$ represents $R^2$, as defined in relation to formula (I), or a group convertible thereto, $A^1$ represents —NO or —NH.CHO and $A^2$ represents —NH.CH$_3$ or —NH$_2$, providing that when $A^1$ is —NO then $A^2$ is —NH.CH$_3$ and when $A^1$ is —NH.CHO then $A^2$ is NH$_2$; and thereafter, if required, carrying out one or more of the following optional steps:

(i) converting any group $R^{1a}$ to $R^1$ and/or $R^{2a}$ to $R^2$;
(ii) converting $R^{3a}$ to $R^3$;
(iii) converting a compound of formula (I) into a further compound of formula (I); and
(iv) if required, forming a pharmaceutically acceptable salt thereof.

The dehydrating cyclisation of a compound of formula (IV) may be carried out under any suitable conditions. Favourably the conditions chosen are these wherein the water formed is removed from the reaction mixture, thus the reaction is generally carried out at an elevated temperature in the range of from 100° C. to 200° C., such as in the range of 180° C. to 190° C.

In one aspect of the process, especially when $A^1$ is —NO and $A^2$ is —NH.CH$_3$, the reaction is carried out in a solvent immiscible with water, such as toluene, at the reflux temperature of the solvent, the water being removed using a water-separator.

Suitable values for $R^{1a}$ and $R^{2a}$ include $R^1$ and $R^2$ respectively.

Suitable groups $R^{1a}$ or $R^{2a}$ convertible to $R^1$ or $R^2$ respectively, include protected forms of the appropriate group $R^1$ or $R^2$ or nitrogen protecting groups such as benzyl groups.

When $R^{1a}$ or $R^{2a}$ represents other than $R^1$ or $R^2$ repectively, the abovementioned conversions of $R^{1a}$ into $R^1$ and $R^{2a}$ to $R^2$ may be carried out using the appropriate conventional procedure. For example when $R^{1a}$ (or $R^{2a}$) represents a nitrogen protecting group, such as a benzyl group, the protecting group may be removed using the appropriate conventional procedure, such as catalytic hydrogenation, and, to effect the formation or $R^1$ (or $R^2$), the resulting product may be reacted with a compound of formula (v):

$$X-(CH_2)_m-A \qquad (V)$$

wherein A and m are as defined in relation to formula (I) and X represents a leaving group, such as halide, for example bromide or iodide.

The last abovementioned conversions may be carried out using conventional alkylation conditions.

Preferably $R^{1a}$ represents $R^1$, especially when $R^1$ represents an unsubstituted hydrocarbon radical of formula (a).

Preferably $R^{2a}$ represents $R^2$, especially when $R^2$ represents an unsubstituted hydrocarbon radical of formula (a).

Suitable values for $R^{3a}$ include $R^3$.

Suitable groups $R^{3a}$ convertible to groups $R^3$ include protected forms of groups $R^3$.

It is particularly suitable that $R^{3a}$ represents a group convertible to $R^3$ for values of $R^3$ such as substituted alkyl, substituted alkenyl or substituted alkynyl or a moiety of formula (a) wherein the group A is a substituted cycloalkyl radical.

Protected forms of groups $R^3$ include those incorporating conventional protecting groups for example acetal or ketal protecting groups, when $R^3$ represents oxoalkyl, or ester protecting groups when $R^3$ represents hydroxyalkyl.

The abovementioned protecting groups may be removed using the appropriate conventional procedures, for example a ketal or acetal group may be removed using mild acid hydrolysis and an ester protecting group may be removed by use of mild basic hydrolysis.

Where appropriate, especially for the preparation of compounds of formula (I) wherein $R^1$ and $R^2$ are different, one of $R^{1a}$ or $R^{2a}$, especially $R^{1a}$, in compound (II) or compound (IV) may represent hydrogen, and the variables $R^{1a}$ and $R^{2a}$ may then be converted independently to $R^1$ and $R^2$ as appropriate.

One preferred form of the process for preparing compounds of formula (I), or where appropriate a pharmaceutically acceptable salt thereof, wherein $R^1$ and $R^2$ are different, comprises the dehydrating cyclisation of a compound of the abovedefined formula (IV) wherein at least one of $R^{1a}$ and $R^{2a}$ represents a protected nitrogen group; and thereafter one nitrogen protecting group is removed and the resulting compound treated with a compound of the abovedefined formula (V); and thereafter, if required, carrying out one or more of the following optional steps:

(i) converting any group $R^{1a}$ to $R^1$ and/or $R^{2a}$ to $R^2$ as necessary;
(ii) converting $R^{3a}$ to $R^3$;
(iii) converting a compound of formula (I) into a further compound of formula (I); and
(iv) if required, forming a pharmaceutically acceptable salt thereof.

Preferably, in the last abovementioned reaction in the compound of formula (IV), $R^{1a}$ represents $R^1$ and $R^{2a}$ represents benzyl.

The abovementioned conversion of a compound of formula (I) into a further compound of formula (I) includes conversions wherein one value of $R^3$ is converted into another value of $R^3$, such as:

(a) converting a compound of formula (I) wherein $R^3$ represents hydrogen into a compound of formula (I) wherein $R^3$ is other than hydrogen;
(b) converting a compound of formula (I) wherein $R^3$ represents an oxoalkyl group into a compound of formula (I) wherein $R^3$ represents a hydroxyalkyl group; and
(c) converting a compound of formula (I) wherein $R^3$ represents an alkenyl group to a compound of formula (I) wherein $R^3$ represents dihydroxyalkyl.

The last abovementioned conversions (a), (b) and (c) may be carried out by means of the appropriate conventional procedure. For example conversion (a) may be carried out under the conditions discussed above for the reaction between compounds of formulae (II) and (III).

Conversion (b) may be carried out by reducing the oxoalkyl group with an appropriate reducing agent such as sodium borohydride, in any suitable solvent, for example methanol, conveniently at ambient temperature.

The abovementioned conversion (c) may be carried out by oxidising the alkenyl group to the epoxide which may be opened hydrolytically to give the required dihydroxyalkyl, or the said alkenyl group may be oxidised directly to the said dihydroxy compound.

Suitable oxidising agents include potassium permanganate, t-butyl hydrogen peroxide, osmium tetroxide and silver benzoate, and epoxide opening may conveniently be effected by treatment with aqueous acid or base.

The protection of any reactive group or atom, such as the xanthine nitrogen atom may be carried out at any appropriate stage in the aforementioned process. Suitable protecting groups include those used conventionally in the art for the particular group or atom being protected, for example suitable protecting groups for the xanthine nitrogen atoms include benzyl and as mentioned above, an oxo group may be protected as a ketal.

Protecting groups may be prepared and removed using the appropriate conventional procedure:

For example, N-benzyl protecting groups may be prepared by treating the appropriate compound of formula (II) with benzyl chloride in the presence of a base such as triethylamine. The N-benzyl protecting groups may be removed by catalytic hydrogenation over a suitable catalyst, such as palladium on activated charcoal, in a suitable solvent, such as ethanol conveniently at an elevated temperature, or by treatment with anhydrous aluminium chloride in dry benzene at ambient temperature.

Also, an oxoalkyl group may be protected as a ketal group by treatment with an appropriate alcohol in an inert solvent, such as xylene, or alternatively by using the alcohol as the solvent, in the presence of an acid catalyst such as p-toluenesulphonic acid, at an elevated temperature. The ketal may be removed by using conventional acid hydrolysis methods.

The compounds of formula (II) may be prepared from compounds of formula (IV) using an analogous procedure to that described above for the preparation of compounds of formula (I). It will be appreciated that certain of the compounds of formula (II), those wherein $R^{1a}$ and $R^{2a}$ represent $R^1$ and $R^2$ respectively, are in fact compounds of formula (I).

A compound of formula (IV) wherein $A^1$ represents —NH.CHO and $R^2$ represents —NH$_2$ may suitably be prepared from a 6-aminouracil of formula (A) according to the following reaction scheme:

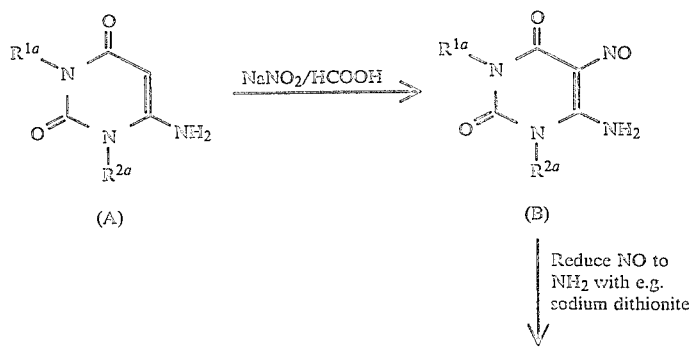

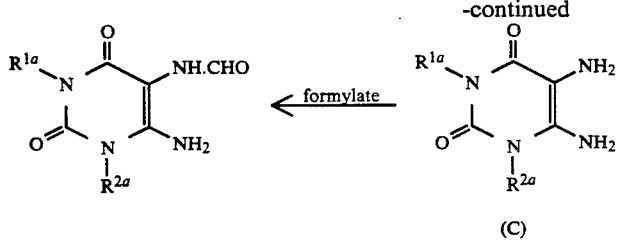

(C)

wherein $R^{1a}$ and $R^{2a}$ are as defined in relation to formula (II).

Suitably, the reaction conditions used in the above-mentioned reaction scheme are appropriate conventional conditions. In a preferred aspect of the process, the conversion of the 6-aminouracil (A), via (B) and (C), to the corresponding compound of formula (IV) and the cyclisation of the compound of formula (IV) to the compound of formula (I) are all carried out in-situ, suitably by using an analogous procedure to that of H. Bredereck and A. Edenhofer, Chem. Berichte 88, 1306–1312 (1955).

The 6-aminouracils of formula (A) may themselves be prepared by the method of V. Papesch and E. F. Schroder, J. Org. Chem., 16, 1879–90 (1951), or Yozo Ohtsuka, Bull. Chem. Soc. Jap., 1973, 46(2), 506–9.

A compound of formula (IV) wherein $A^1$ represents —NO and $A^2$ represents —NH.CH$_3$ may conveniently be prepared from a 6-chlorouracil of formula (D), according to the following reaction scheme:

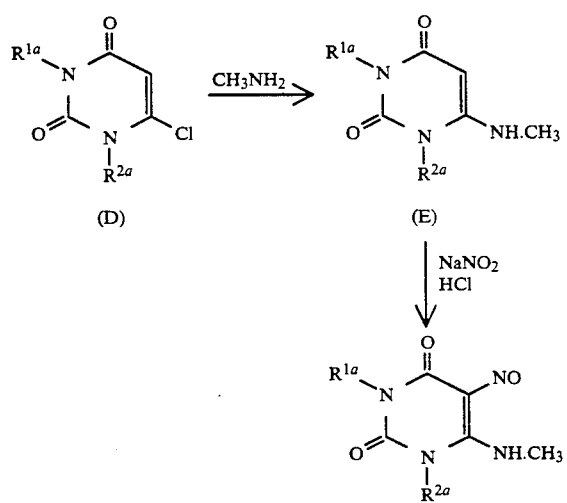

wherein $R^{1a}$ and $R^{2a}$ are as defined in relation to formula (II).

Suitably, the reaction conditions used in the above mentioned scheme are the appropriate conventional conditions, for example those used in the method of H. Goldher, G. Dietz and E. Carstens, Liebigs Annalen der Chemie, 691, 142–158 (1965). The 6-chlorouracil of formula (D) may also be prepared according to the procedure of Dietz et al.

The compounds of formula (II) are useful as intermediates, and accordingly form part of the present invention. Certain of the compounds of formula (II) possess pharmacological activity similar to that of the above-mentioned compounds of formula (I), especially those compounds of formula (II) ('the relevant subgroup') wherein $R^{1a}$ represents $R^1$, $R^{2a}$ represents benzyl and $R^{3a}$ represents $R^3$. Accordingly, the present invention provides the compounds of formula (II), especially the relevant sub-group; and in addition pharmaceutical compositions comprising these compounds and methods of treatment and uses of these compounds (analogous to the compositions, methods and uses mentioned herein in relation to the compounds of formula (I)) are encompassed herein.

The present invention also provides a pharmaceutical composition comprising a compound of formula (I), or where appropriate a pharmaceutically acceptable salt thereof, and a pharmaceutically acceptable carrier. The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing.

Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (I), or where appropriate a pharmaceutically acceptable salt thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (I) or if appropriate a pharmaceutically acceptable salt thereof, are conventional formulations well known in the art, for example, as described in standard text books of pharmaceutics and cosmetics, such as Harry's Cosmeticology published by Leonard Hill Books, Remington's Pharmaceutical Sciences, and the British and US Pharmacopoeias.

Suitably, the compound of formula (I), or where appropriate a pharmaceutically acceptable salt thereof, will comprise from about 0.5 to 20% by weight of the formulation, favourably from about 1 to 10%, for example 2 to 5%.

The invention also provides a method for the treatment of cerebrovascular disorders and/or disorders associated with cerebral senility in mammals, including humans, which comprises administering to the sufferer an effective, non-toxic amount of a compound of formula (I), or where appropriate a pharmaceutically acceptable salt thereof.

The invention further provides a method of treatment in mammals, including humans of cerebral vascular and neuronal degenerative disorders associated with learning, memory and cognitive dysfunctions including cerebral senility, multi-infarct dementia and senile dementia of the Alzheimer type, which comprises administering to the sufferer an effective, non-toxic amount of a compound of formula (I), or where appropriate a pharmaceutically acceptable salt thereof.

The invention further provides a method for the treatment of peripheral vascular disease in mammals including humans, which comprises administering to the sufferer an effective, non-toxic amount of a compound of formula (I), or where appropriate a pharmaceutically acceptable salt thereof.

In yet a further aspect, the present invention provides a method for the treatment of disorders resulting from an ischaemic event in mammals, especially humans, which method comprises the administration to the sufferer of an effective, non-toxic, amount of the compound of formula (I), or where appropriate a pharmaceutically acceptable salt thereof.

Relevant ischaemic events include cerebral ischaemia caused by cardiac arrest and by stroke and also includes the cerebral ischaemia which may result from surgery.

Also to be mentioned is the cerebral ischaemia which may occur in newborns during birth.

In one aspect the disorders resulting from the ischaemic event includes disorders associated with neuronal degeneration following the ischaemic event.

In a further distinct but related aspect, the disorders resulting from the ischaemic event includes functional disorders resulting from disturbed brain function following the ischaemic event, such as speech and locomotive disorders, sensory disorders, the loss of social skills and other such behavioural disorders associated with the post-ischaemic period.

In another aspect, the present invention provides a method for the treatment of proliferative skin disease in mammals including humans which comprises administering to the mammal in need of such treatment an effective amount of a compound of formula (I), or where appropriate a pharmaceutically acceptable salt thereof.

The present invention also provides a method for the treatment of reversible airways obstruction and asthma in mammals including humans which comprises administering to the mammal in need of such treatment an effective amount of a compound of formula (I), or where appropriate a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.5 to 1000 mg. for example 0.5 to 200 mg; and such unit doses may be administered more than once a day, for example two or three times a day, so that the total daily dosage for a 70 kg adult is in the range of about 1 to 1000 mg, that is in the range of about 0.02 to 20 mg/kg/day; and such therapy may extend for a number of weeks or months.

At the above described dosage range, no toxicological effects are indicated for the compounds of the present invention.

In a further aspect the invention provides a compound of formula (I), or where appropriate a pharmaceutically acceptable salt thereof, for use as an active therapeutic substance.

The invention further provides a compound of formula (I), or where appropriate a pharmaceutically acceptable salt thereof, for use in the treatment of cerebral vascular and neuronal degenerative disorders associated with learning, memory and cognitive dysfunctions including cerebral senility, multi-infarct dementia and senile dementia of the Alzheimer type and/or disorders resulting from an ischaemic event and/or peripheral vascular disease and/or proliferative skin diseases and/or reversible airways obstruction and/or asthma.

In another aspect, the invention provides the use of a compound of formula (I), or where appropriate a pharmaceutically acceptable salt thereof, for the manufacture of a medicament for the treatment of cerebral vascular and neuronal degenerative disorders associated with learning, memory and cognitive dysfunctions including cerebral senility, multi-infarct dementia and senile dementia of the Alzheimer type and/or disorders resulting from an ischaemic event and/or peripheral vascular disease and/or proliferative skin diseases and/or reversible airways obstruction and/or asthma.

The following examples illustrate the invention and the following preparations illustrate the preparation of intermediates thereto.

EXAMPLE 1

1,3-Di-cyclopropylmethyl xanthine 1,3-Di-cyclopropylmethyl xanthine was prepared using an analogous procedure to that described in Chem. Berichte 88, 1306–1312, 1955: 20.2 g (0.0855 mol) of 1,3-di-cyclopropylmethyl-6-amino-uracil was dissolved in 100 ml of formamide, then 5.9 g sodium nitrite was added and at 60° C. 13.4 ml formic acid was added slowly with stirring. After the colour had changed from yellow to violet, the mixture was heated up to 100° C. and 3.1 g of sodium dithionite ($Na_2S_2O_4$) was added in small portions.

Then the mixture was heated to 180°–190° C. and held at this temperature for 30 minutes.

After cooling, the precipitate was sucked off, washed with 50 ml of water and recrystallised from toluene. Yield: 22.5 g, m.p. 203° C.

$^1$H NMR ($CDCl_3$):

ppm: 0.44–0.54 (8H, q); 1.18–1.57 (2H, m); 3.98–4.12 (4H, 2d); 7.81 (1H, s); 12.8–13.2 (1H, s, exch. with $D_2O$).

EXAMPLE 2

1,3-Di-cyclobutylmethyl xanthine 1,3-Di-cyclobutylmethyl xanthine was prepared from 1,3-dicyclobutylmethyl-6-aminouracil using an analogous procedure to that described in Example 1. The title compound was isolated as a crystalline solid, m.p. 191° C.

$^1$H NMR ($CDCl_3$).:

ppm: 1.6–2.3 (12H, m); 2.4–3.2 (2H, m); 4.16 (2H, d, J=7.0Hz); 4.21 (2H, d, J=7.3Hz); 7.76 (1H, d, J=1.3Hz, exch. with $D_2O$ to give s) 12.7 (1H, br.s, exch. with $D_2O$).

EXAMPLE 3

1,3-Di-cyclopentylmethyl xanthine 1,3-Di-cyclopentylmethyl xanthine was prepared from 1,3-di-cyclopentylmethyl-6-aminouracil using an analogous procedure to that described in Example 1. The title compound was isolated as a crystalline solid, m.p. 208° C.

$^1$H NMR ($CDCl_3$):

ppm: 1.0–2.0 (16H, m); 2.2–2.9 (2H, m); 4.0–4.3 (4H, m); 7.78 (1H, d, J=1.2Hz, exch. with $D_2O$ to give s; 12.9 (1H, br.s, exch. with $D_2O$).

EXAMPLE 4

1,3-Di-cyclohexylmethyl xanthine 1,3-Di-cyclohexylmethyl xanthine was prepared from 1,3-di-cyclohexylmethyl-6-aminouracil using an analogous procedure to that described in Example 1. The title compound was isolated as a crystalline solid, m.p. 237° C.

$^1$H NMR ($CDCl_3$):

ppm: 0.8–2.2 (22H, m); 3.85–4.15 (4H, m (dd)); 7.73 (1H, s); 13.1 (1H, br.s, exch. with $D_2O$).

EXAMPLE 5

1,3-Di-cyclooropylmethyl-7-(2-oxopropyl)-xanthine 1,3-Di-cyclopropylmethyl-7-(2-oxopropyl)-xanthine, m.p. 161° C., was prepared using an analogous procedure to that disclosed in United Kingdom Patent No. 1,441,562: 5.2 g (0.02 mol) of 1,3-di-cyclopropylmethyl xanthine was refluxed with 50 ml toluene, 4 g triethylamine and 24 mg sodium iodide for 5 minutes. Then 3.7 ml of chloroacetone was added slowly in two portions over 3 hours while the reaction mixture was under reflux. After cooling 22 ml of water was added, the organic layer separated and washed twice, each time with 20 ml of a 2.5N sodium hydroxide solution.

Then the organic layer was washed with 50 ml of water and dried over anhydrous sodium sulphate.

After concentration, the precipitate was sucked off and washed with petrol-ether.

Yield: 3.3 g, 52% approx.

$^1$H NMR ($CDCl_3$):

ppm: 0.39–0.54 (8H, m); 1.18–1.46 (2H, m); 2.33 (3H, s); 3.82–4.04 (4H, 2 x d); 5.16 (2H, s); 7.52 (1H, s).

EXAMPLE 6

1,3-Di-cyclobutylmethyl-7-(2-oxopropyl)-xanthine 1,3-Di-cyclobutylmethyl-7-(2-oxopropyl)-xanthine was prepared from 1,3-di-cyclobutylmethyl xanthine and chloroacetone using an analogous procedure to that described in Example 5. The title compound was isolated as a crystalline solid, m.p. 155° C.

$^1$H NMR ($CDCl_3$)

ppm: 1.6–2.2 (12H, m); 2.3 (3H, s); 2.4–3.1 (2H, m); 4.13 (2H, d, J=7.2Hz); 3.99 (2H, d, J=7.1Hz); 5.09 (2H, s); 7.43 (1H, s).

EXAMPLE 7

1,3-Di-cyclopentylmethyl-7-(2-oxopropyl)-xanthine 1,3-Di-cyclopentylmethyl-7-(2-oxopropyl)-xanthine was prepared from 1,3-di-cyclopentylmethyl xanthine and chloroacetone using an analogous procedure to that described in Example 5. The title compound was isolated as a crystalline solid, m.p. 144° C.

$^1$H NMR ($CDCl_3$):

ppm: 1.1–2.0 (16H, m); 2.2–2.8 (SH, m); 3.85–4.2 (4H, m); 5.15 (2H, s); 7.5 (1H, s).

EXAMPLE 8

1,3-Di-cyclohexylmethyl-7-(2-oxopropyl)-xanthine 1,3-Di-cyclohexylmethyl-7-(2-oxopropyl)-xanthine was prepared from 1,3-di-cyclohexylmethyl xanthine and chloroacetone using an analogous procedure to that described in Example 5. The title compound was isolated as a crystalline solid, m.p. 153° C.

$^1$H NMR ($CDCl_3$):

ppm: 0.75–2.2 (22H, m); 2.32 (3H, s); 3.83 (2H, d, J=7Hz); 3.95 (2H, d, J=7.2Hz); 5.15 (2H, s); 7.51 (1H, s).

EXAMPLE 9

1,3-Di-cyclopentylmethyl-7-(2-hydroxypropyl)-xanthine 1,3-Di-cyclopentylmethyl-7-(2-oxopropyl)-xanthine was dissolved in methanol and stirred for 2 hours at room temperature with 5 equivalents of sodium borohydride. Thereafter, the solvent was removed in vacuo and the residue partitioned between dichloromethane and water. The organic layer was then separated and dried over sodium sulphate. After removing the organic solvent the title compound was crystallised from absolute ethanol as a white crystalline solid, m.p. 139° C.

$^1$H NMR (CDCl$_3$):
ppm: 1.1–2.0 (19H, m); 2.1–2.8 (2H, m); 2.95 (1H, d, J=2.2Hz, exch. with D$_2$O); 3.8–4.6 (7H, m); 7.59 (1H,s).

EXAMPLE 10

1,3-Di-cyclohexyl xanthine 1,3-Di-cyclohexyl xanthine was prepared using an analogous procedure to that described in Liebigs Annalen der Chemie 691, 142–158, (1965):

a) 1,3-Di-cyclohexyl-6-chloro-uracil: A mixture of 2.9 g (0.01 mol) 1,3-di-cyclohexyl-barbituric acid, 20 ml of phosphoryl chloride and 0.1 g of ortho-phosphoric acid (H$_3$PO$_4$) were refluxed for 2 hours with stirring. After removal of excess phosphoryl chloride by distillation, the oily residue was treated with iced-water and extracted with dichloromethane.

After drying over anhydrous sodium sulphate and removal of the solvent in vacuo, 2.7 g of crude oily 1,3-di-cyclohexyl-6-chloro-uracil was isolated which was then used without further purification.

b) 1.3-Di-cyclohexyl-6-methylaminouracil: The oily 1,3-di-cyclohexyl-6-chloro-uracil was dissolved in 10 ml of absolute ethanol and treated with 2.5 ml of an aqueous methylamine-solution (40% w/w) at 70° C. for 30 minutes.

After cooling, the mixture was treated under stirring with an additional 20 ml of water, the precipitate was sucked off and dissolved in hot methanol. After removal of some insoluble material, the solution was concentrated and 1,3-di-cyclohexyl-6-methylaminouracil crystallised from diethylether. Yield: 0.7 g, 23% approx., m.p. 222° C.

c) 1,3-Di-cyclohexyl-xanthine: 0.38 g (0.0055 mol) of sodium nitrite was dissolved in 5.6 ml of methanol. After adding 1.5 g (0.005 mol) of 1,3-di-cyclohexyl-6-methylaminouracil, 0.54 ml of concentrated hydrochloric acid was dropped into the stirred mixture.

After stirring for 1 hour, 50 ml of water was added and the product extracted with 80 ml of toluene. After drying over anhydrous sodium sulphate, the toluene-solution was refluxed in a water-separator for 2 hours.

The cooled solution was extracted with 50 ml 1N sodium hydroxide and then with 30 ml of water. After filtration the aqueous phase was acidified to pH 2. The white precipitate was sucked off and washed with water. This purification procedure was then repeated (i.e. product dissolved in alkali and crystallised acidic medium) and the product further recrystallised twice from diethylether.

Yield: 0.3 g, 20%. Mpt.: 140° C.

$^1$H NMR (CDCl$_3$):
ppm: 1.0–2.15 (16H, m); 2.15–2.85 (4H, m); 4.55–5.2 (2H, m); 7.74 (1H, s); 12.5 (1H, br.s, exch. with D$_2$O).

EXAMPLE 11

1,3-Di-cyclohexyl-7-(2-oxopropyl)-xanthine 1,3-Di-cyclohexyl-7-(2-oxopropyl)-xanthine was prepared from 1,3-di-cyclohexyl xanthine and chloroacetone using an analogous procedure to that described in Example 5. The title compound was isolated as a crystalline solid, m.p. 185° C.

$^1$H NMR (CDCl$_3$):
ppm: 1.0–2.1 (16H, m); 2.1–2.8 (7H, m); 4.5–5.0 (2H, m); 5.14 (2H, s); 7.46 (1H, s).

EXAMPLE 12

1,3-Di-cyclobutylmethyl-7-(2-hydroxypropyl)-xanthine 1,3-Di-cyclobutylmethyl-7-(2-hydroxypropyl)-xanthine was prepared from 1,3-di-cyclobutylmethyl-7-(2-oxo-propyl)-xanthine using an analogous procedure to that described in Example 9. The title compound was isolated as a crystalline solid, m.p. 122° C.

$^1$H NMR (CDCl$_3$):
ppm: 1.26 (3H, d, J=5.9Hz); 1.7–2.25 (12H, m); 2.25–3.1 (3H, m, exch. with D$_2$O); 3.9–4.65 (7H, m); 7.57 (1H, s).

EXAMPLE 13

1,3-Di-cyclobutyl-xanthine 1,3-Di-cyclobutyl-xanthine was prepared from 1,3-dicyclobutyl-6-amino-uracil using an analogous procedure to that described in Example 1. The title compound was isolated as a crystalline solid, m.p. 173° C.

$^1$H NMR (CDCl$_3$):
ppm: 1.6–2.6 (8H, m); 2.8–3.5 (4H, m); 5.0–5.7 (2H, m); 7.77 (1H, s); 12.6 (1H, br.s).

EXAMPLE 14

1,3-Di-cyclopropylmethyl-7-n-propyl xanthine 1,3-Di-cyclopropylmethyl-7-n-propyl xanthine was prepared from 1,3-di-cyclopropylmethyl xanthine and 1-chloropropane using an analogous procedure to that described in Example 5. The title compound was isolated as a crystalline solid, m.p. 67° C.

$^1$H NMR (CDCl$_3$):
ppm: 0.35–0.65 (8H, m); 0.96 (3H, t, J=7.3Hz); 1.1–1.65 (2H, m); 1.7–2.2 (2H, m); 3.8–4.4 (6H, m); 7.49 (1H, s).

EXAMPLE 15

1,3-Di-cyclobutylmethyl-7-n-propyl xanthine 1,3-Di-cyclobutylmethyl-7-n-propyl xanthine was prepared from 1,3-di-cyclobutylmethyl xanthine and 1-chloropropane using an analogous procedure to that described in Example 5. The title compound was isolated as a crystalline solid, m.p. 91° C.

$^1$H NMR (CDCl$_3$):
ppm: 0.95 (3H, t, J=7.3Hz); 1.5–2.25 (14H, m); 2.6–3.05 (2H, m); 3.95–4.8 (6H, m); 7.49 (1H, s).

EXAMPLE 16

1,3,7-Tri-cyclopropylmethyl-xanthine 1,3-Tri-cyclopropylmethyl-xanthine was prepared from 1,3-di-cyclopropylmethyl xanthine and cyclopropylchloromethane using an analogous procedure to that described in Example 5. The title compound was isolated as a crystalline solid, m.p. 78° C.

$^1$H NMR (CDCl$_3$):

ppm: 0.35–0.8 (12H, m); 1.1–1.6 (3H, m); 3.85–4.3 (6H, m); 7.63 (1H, m).

EXAMPLE 17

1-(Cyclopropylmethyl)-3-cyclopentyl-7-(3-oxobutyl)-xanthine 5 g of 1-(cyclopropylmethyl)-7-(3-oxobutyl)xanthine were stirred at 60° C. for 2 hours with 3.8 g of cyclopentylbromide and 3.5 g potassium carbonate in 20 ml dimethylformamide (DMF). The mixture was neutralized with hydrochloric acid and the solvent was evaporated. The residue was taken up in water/ethyl acetate and extracted into the ethyl acetate. The product was then purified by column-chromatography (ether).

$^1$H NMR (CDCl$_3$):

δ: 7.61(1H, s); 5.15(1H, m); 4.39(2H, t, J=7); 3.90(2H, d, J=7); 2,94(2H, t, J=7); 2.19(3H, s); 1.90(8H, m); 1.30(1H, m); 0.40(4H, m).

EXAMPLE 18

1-(Cyclopropylmethyl)-3-cyclopentylxanthine 1-(Cyclopropylmethyl)-3-cyclopentyl-7-(3-oxobutyl)-xanthine, 600 mg, was treated with 200 mg of potassium hydroxide in 10 ml ethanol at room temperature for 1 hour. The solvent was then evaporated. Water was added to the residue and the product was extracted with ethyl acetate. The organic layer was washed with water, dried over anhydrous sodium sulphate and the solvent was evaporated. The product was crystallised from acetone, m.p.: 178° C.

$^1$H NMR (d$_6$- DMSO):

δ: 11.85(1H, s, exch. with D$_2$O); 8.13(1H s); 5.05(1H m); 3.79(2H, d, J=7); 2.00(8H m); 1.25(1H, m); 0.40(4H, m).

calc. C 61.30% H 6.61% N 20.42% O 11.66% found. C 61.22% H 6.68% N 20.36% O 11.70%

EXAMPLE 19

1-(Cyclopropylmethyl)-3-(cyclohexylmethyl)-7-(2-oxopropyl)xanthine 1-(Cyclopropylmethyl)-7-(2-oxopropyl)xanthine, 1.5 g was dissolved in 20 ml DMF and then 825 mg of potassium carbonate and 1.5 ml bromomethylcyclohexane were added. The mixture was stirred for 2 hours at 80° C. After cooling, water was added and the product was extracted with ethyl acetate. The organic layer was dried and the solvent evaporated. The product crystallised from ether, m.p. 144° C.

$^1$H NMR (CDCl$_3$):

δ: 7.51(1H, S); 5.15(2H, s); 3.91(4H, dd, J=7); 2.33(3H, s); 0.8–2.2(12H, m); 0.40(4H, m).

calc. C 63.67 H 7.31 N 15.63 O 13.39
found. C 63.64 H 7.32 N 15.64 O 13.40

EXAMPLE 20

1-(Cyclopropylmethyl)-3-cyclopentyl-7-(2-oxopropyl)-xanthine

The title compound was prepared from 1-cyclopropylmethyl-7-(2-oxopropyl)xanthine and cyclopentylbromide in an analogous procedure to that of Example 19. The product was obtained as a crystalline solid; m.p. 155° C.

$^1$H NMR(CDCl$_3$):

δ: 7.48 (1H, s); 5.25 (1H, m); 5.14 (2H, s); 3.85 (2H, d, J=7); 2.32 (3H, s); 2.00 (8H, m); 1.27 (1H, m).; 0.4 (4H, m).

Calc. C 61.80 H 6.71 N 16.96 O 14.53
Found. C 61.74 H 6.74 N 16.94 O 14.56

EXAMPLE 21

1-(Cyclopropylmethyl)-3-cyclohexylmethyl-7-(3-oxobutyl)xanthine

The title compound was prepared by stirring 1-cyclopropylmethyl-7-(3-oxobutyl)xanthine, 5 g, with 4.6 mls of bromomethylcyclohexane and 5.2 g of potassium carbonate in 30 ml DMF over 5 hours. After evaporation of the solvent the title compound was purified by column chromatography (ether).

EXAMPLE 22

1-(Cyclopropylmethyl)-3-(cyclohexylmethyl)xanthine

This was prepared from the compound of Example 21, 900 mg, by treating with 200 mg potassium hydroxide in 10 ml of ethanol for 1 hour at room temperature. The title compound was isolated in an analogous manner to Example 18, m.p. 181° C.

$^1$H NMR (d6-DMSO):

δ: 11.85 (1H, s, exch. with D$_2$O); 8.01 (1H, s); 4.15 (2H, d, J=7); 3.79 (2H, d, J=7); 1.40 (12H, m); 0.40 (4H, m).

Calc. C 63.55 H 7.33 N 18.53 O 10.58
Found. C 63.62 H 7.32 N 18.51 O 10.64

PREPARATION 1

N,N'-Di-cyclopropylmethyl urea

N,N'-Di-cyclopropylmethyl urea, m.p. 124° C., was prepared using a procedure analogous to that described in J. Org. Chem. 16, 1879–1890, (1951):

68.2 g (0.634 mol) cyclopropylmethylamine-hydrochloride in 800 ml of water was treated with 25 g sodium hydroxide dissolved in 100 ml of water and the mixture cooled to −15° C.

Phosgene, 33 g was then slowly introduced through a capillary tube with stirring. Thereafter the mixture was stirred for 1 hour and, as necessary, after acidification with 0.1N HCl, the product was extracted with dichloromethane.

After washing with water and drying over anhydrous sodium sulphate the product was obtained after evaporation of the solvent.

Yield: 21 g, 40% approx.

From the aqueous phase, 20 g of the unreacted aduct (cyclopropylmethylamine-hydrochloride) can be obtained.

$^1$H NMR (CDCl$_3$):

ppm: 0.06–0.59 (8H, m); 0.72–1.06 (2H, m); 3.01–3.09 (4H, d); 4.66 (1H, br.s, exch. with D$_2$O).

PREPARATION 2

N,N'-Di-cyclobutylmethyl urea

N,N'-Di-cyclobutylmethyl urea was prepared from cyclobutylmethylamine using a procedure analogous to that described in Preparation 1. The title compound was isolated as a crystalline solid, m.p. 155° C.

$^1$H NMR (CDCl$_3$):

ppm: 1.4–2.8 (14H, m); 3.0–3.3 (4H, m); 4.59 (2H, br.s, exch. with D$_2$O).

PREPARATION 3

N,N'-Di-cyclopentylmethyl urea

N,N'-Di-cyclopentylmethyl urea was prepared from cyclopentylmethylamine using a procedure analogous to that described in Preparation 1. The title compound was isolated as a crystalline solid, m.p. 150° C.

$^1$H NMR (CDCl$_3$):
ppm: 1.0–2.2 (18H, m); 2.9–3.2 (4H, m); 4.59 (2H, br.s, exch. with D$_2$O).

PREPARATION 4

N,N'-Di-cyclohexylmethyl urea

N,N'-Di-cyclohexylmethyl urea was prepared from cyclohexylmethylamine using a procedure analogous to that described in Preparation 1. The title compound was isolated as a crystalline solid, m.p. 159° C.

PREPARATION 5

1,3-Di-cyclopropylmethyl-6-aminouracil 1,3-Di-cyclopropylmethyl-6-aminouracil was prepared using an analogous procedure to that described in J. Org. Chem. 16, 1879–1890, (1951):

22.6 g (0.138 mol) of the N,N'-dicyclopropylmethyl-urea (from Preparation 1) was treated with 44 ml (0.43 mol) of acetic anhydride and 14 g (0,165 mol) of cyanocetic-acid at 70° C. for 2 hours.

After cooling and the addition of 15 ml of water, 40 ml of 50% NaOH/water-solution was dropped slowly onto the mixture at 45° C. with stirring.

After stirring for 1 hour at room temperature, the strongly alkaline solution was separated and the oily residue washed carefully with 60 ml water.

The semi-solid residue was dissolved in 220 ml methanol and dropped into 1 litre of water with stirring. Thereby the product crystallised. Yield: 25.5 g, 78.5% approx., m.p. 85°–95° C. (wax-like).

PREPARATION 6

1,3-Di-cyclopentylmethyl-6-aminouracil 1,3-Di-cyclopentylmethyl-6-aminouracil was prepared from N,N'-di-cyclopentylmethyl urea using a procedure analogous to that described in Preparation 5. The title compound was isolated as a crystalline solid, m.p. 108° C.

$^1$H NMR (CDCl$_3$):
ppm: 1.0–2.6 (18H, m); 3.86 (4H, d, J=7.4H$_z$); 4.98 (3H, m, 2H exch. with D$_2$O).

PREPARATION 7

1,3-Di-cyclohexylmethyl-6-aminouracil 1,3-Di-cyclohexylmethyl-6-aminouracil was prepared from N,N'-di-cyclohexylmethyl urea using a procedure analogous to that described in Preparation 5. The title compound was isolated as a crystalline solid, m.p. 185° C.

PREPARATION 8

3-Benzyl-7-(3-oxobutyl)xanthine

3-Benzylxanthine (Bull. Chem. Soc. Jap. 1973, 46(2), 506–9) 93.3 g, was dissolved in 1.7l of DMF and 16 ml of triethylamine were added. 42.5 ml of methyl vinylketone were then dropped into the mixture and the mixture was stirred for 24 hours. The solvent was evaporated, and the product was used without further purification.

$^1$H NMR (d$_6$- DMSO):
δ: 11.30(1H, s, exch. with D$_2$O): 8.04(1H, s); 7.37(5H, s); 5.15(2H, s); 4.43(2H, t, J=6.7); 3.15(2H, t, J=6.7); 2.16(3H, s).

PREPARATION 9

1-(Cyclopropylmethyl)-3-benzyl-7-(3-oxobutyl)xanthine 6.2 g of 3-benzyl-7-(3-oxobutyl)xanthine were dissolved in 120 ml of DMF. 5.8 ml of bromomethylcyclopropane and 6.8 g potassium carbonate were added. The mixture was stirred overnight and then poured into water and extracted with ethyl acetate. The organic solvent was evaporated and the product was purified by column chromatography (ether).

$^1$H NMR (CDCl$_3$):
δ: 7.67(1H, s); 7.40(5H, m); 5.26(2H, s); 4.48(2H, t, J=6); 3.90(2H, d, J=7); 3.07(2H, t, J=6); 2.13(3H, s); 1.25(1H, m); 0.45(4H, m).

PREPARATION 10

1-(Cyclopropylmethyl)-7-(3-oxobutyl)xanthine 36 g of 1-(cyclopropylmethyl)-3-benzyl-7-(3-oxobutyl)-xanthine were hydrogenated in 300 ml isopropanol and 1 ml of concentrated hydrochloric acid using 3 g of Pd/C catalyst at 2 bar and 60° C. for 12 hours. The catalyst was filtered off, the solvent evaporated and the product was purified by column chromotagraphy.

$^1$H NMR (d$_6$- DMSO):
δ: 11.9(1H, s, exch. with D$_2$O); 8.02(1H, s); 4.45(2H, t, J=6.7); 3.85(2H, d,J=7); 3.13(2H,t, J=6.7); 2.17(3H, s); 1.25(1H, m); 0.45(4H, m).

PREPARATION 11

3-Benzyl-7-(2-oxopropyl)-xanthine 24 g of 3-benzylxanthine were dissolved in 300 ml dimethylsulphoxide/ethanol (1.1). 8 g of sodium ethylate and 18 ml chloroacetone were added and the mixture was stirred overnight. The precipitate was filtered off, washed with 3 portions of water and then with 3 portions of ethanol.

$^1$H NMR (d$_6$- DMSO):
δ: 11.25(1H, s, exch. with D$_2$O); 7.97(1H, s); 7.38(5H, s); 5.28(2H, s); 5.17(2H, s); 2.27(3H, s).

PREPARATION 12

1-(Cyclopropylmethyl)-3-benzyl-7-(2-oxopropyl)xanthine 18.1 g of 3-benzyl-7-(2-oxopropyl)xanthine were treated with 11.4 ml of bromomethylcyclopropane and 9.2 g of potassium carbonate in 150 ml of DMF for 3 hours at 70° C. The mixture was concentrated, water was added and the product was extracted with ethyl acetate. After concentration of the solution the product crystallised, m.p. 138° C.

$^1$H NMR(CDCl$_3$):
δ: 7.51(1H, s); 7.40(5H, m); 5.29(2H, s); 5.13(2H, s); 3.86(2H, d, J=7); 2.31(3H, s); 1.25(1H, m); 0.40(4H, m).
calc. C 64.76 H 5.72 N 15.90 O 13.62
found C 64.74 H 5.74 N 15.84 O 13.64

PREPARATION 13

1- (Cyclopropylmethyl)-7-(2-oxopropyl)xanthine 3.6 g of 1-(cyclopropylmethyl)-3-benzyl-7-(2-oxopropyl)xanthine were dissolved in 40 ml of ethanol and then heated to 80° C. 0.5 ml of concentrated hydrochloric acid and 3 g of Pd/C were added. The mixture was stirred for 24 hours in an atmosphere of hydrogen after which the catalyst was filtered off. On cooling the product crystallised. It was recrystallised from acetone, m.p. 239° C.

¹H NMR (CDCl₃):

δ: 9.80(1H,s, exch. with D₂O); 7.55(1H, s); 5.14(2H, s); 3.85(2H, d, J=7); 2.32(3H, s); 1.28(1H, m); 0.45(4H, m).

calc. C 54.96 H 5.38 N 21.36 O 18.30
found C 55.00 H 5.38 N 21.39 O 18.33

PHARMACOLOGICAL DATA

1. INHIBITION OF CYCLIC AMP PHOSPHODIESTERASE

Procedure

The procedure used was that described by Arch, J. R. S. and Newsholme, E. A. in Biochem. J. 158, 603, (1976):

Erythrocytes were obtained from Na-citrate (16 mM; 0.1 ml/ml blood) anticoagulated blood by repeated centrifugation with removal of the buff coat and washing with an isotonic buffer (composition in mM: NaCl 13.7, KCl 4, CACl₂.2 H₂O 1.8, Na₂HPO₄.12 H₂O 0.8, NaH₂PO₄ 0.2, MgSO₄.7 H₂O 0.7, Hepes 3.4; pH 7.4).

The phosphodiesterase was extracted by mixing the erythrocytes with 4 volumes of 7 mM phosphate buffer, pH 7.4, followed by sonification (3×10 sec; 100 W) and then centrifuging for 30 min at 4200 x g.

All supernatants were diluted in the extraction medium and assayed for phosphodiesterase activity within 6 hours of preparation, using the radiochemical procedure described in the above mentioned reference.

Results

| Example No. | Ki [μM] c-AMP phosphodiesterase (erythrocytes) |
|---|---|
| 1 | 5.7 |
| 2 | 2.2 |
| 3 | 3.7 |
| 4 | 1.7 |
| 5 | 1.4 |
| 6 | 0.15 |
| 7 | 1.3 |
| 8 | 2.3 |
| 9 | 26.6 |
| 10 | 0.8 |
| 11 | 2.4 |
| 12 | 13.5 |
| 13 | 1.7 |
| 14 | 5.27 |
| 15 | 2.4 |
| 16 | 2.3 |
| 18 | 8.4 |
| 19 | 2.3 |
| 20 | 2.0 |
| 22 | 23 |

2. DELAYED NEURONAL DEATH IN GERBILS AFTER TRANSIENT FOREBRAIN ISCHAEMIA

Method

Ischaemia was produced in adult male gerbils by occlusion of both common carotid arteries for 3 minutes under halothane/nitrous oxide anaesthesia. During surgery the animals were placed upon a warming blanket. The ischaemia led to neuronal degeneration and to disturbed brain function.

Results

Brains were removed 2 weeks later and 12 μm thick coronal slices were examined light microscopically for neuronal degeneration.

Three groups of animals were used:
1. sham ligated controls
2. solvent-treated ligated controls
3. compound-treated ligated animals The compound was administered 1 hour before the ligation period.

Results

Means±SEM (n) of histopathological score [HPS] which reflects the degree of neuronal damage in the hippocampal CA1 field:
0=no damaged neurons
1=mild necrosis
2=moderate necrosis
3=severe necrosis
4=complete necrosis

|  | Dose mg/kg | HPS | No of animals |
|---|---|---|---|
| sham ligated controls | — | 0 | (4) |
| controls ligated animals: |  |  |  |
| Solvent | — | 3.4 ± 0.3 | (21) |
| Compound of Example 1 | 5.0 i.p. | 2.3* ± 0.6 | (10) |

*significantly different (p < 0.05) from solvent treated ligated animals.

Conclusion

The compound example 1 significantly prevented ischaemia induced neuronal degeneration.

Toxicology:

No toxicological effects were indicated in any of the abovementioned tests.

We claim:

1. A compound of formula (I):

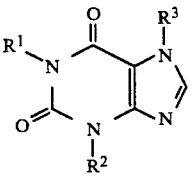

or where appropriate a pharmaceutically acceptable salt thereof, wherein R¹ and R² each independently represents a moiety of formula (a):

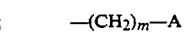

—(CH₂)ₘ—A     (a)

wherein m represents an integer 1, 2, or 3, A represents an unsubstituted C₃₋₈ cycloalkyl or C₃₋₈ cycloalkyl optionally substituted with C₁₋₁₂ alkyl or halogen; and R³ represents hydrogen, C₁₋₆ alkyl, C₂₋₆ alkenyl, C₂₋₆ alkynyl optionally substituted with up to three substituents selected from the group consisting of oxo or a pharmaceutically acceptable acetal thereof provided by a C₁₋₆ alkanol or a ketal thereof provided by 1,2-dihydroxyethane or 1,3-dihydroxypropane, hydroxy or a pharmaceutically acceptable ester thereof provided by a C₁₋₆ carboxylic acid, halogen and nitrile or a moiety of formula (a) as defined above.

2. A method for the treatment of disorders resulting from an ischaemic event and/or peripheral vascular disease and/or psoriasis, atopic dermatitis, irritant contact dermatitis, allergic contact dermatitis, lamellar ichthyosis, epidermolytic hyperkeratosis, premalignant sun induced keratosis, non-malignant keratosis, acne, seborrheic dermatitis, and mange and/or reversible airways obstruction and asthma, in mammals, which comprises administering to the mammal in need of such treatment an effective, non-toxic amount of a compound of formula (I), or where appropriate a pharmaceutically acceptable salt thereof.

3. A compound according to claim 1, wherein A represents an unsubstituted $C_{3-6}$ cycloalkyl group.

4. A compound according to claim 1, wherein A represents cyclopropyl.

5. A compound according to claim 1, wherein m represents 1.

6. A compound according to claim 1, wherein $R^3$ represents substituted $C_{1-6}$ alkyl.

7. A compound according to claim 1, wherein $R^3$ represents a 2-oxopropyl group.

8. A compound according to claim 1, wherein $R^3$ represents hydrogen.

9. A compound according to claim 1, selected from the group consisting of:
1,3-di-cyclopropylmethyl xanthine;
1,3-di-cyclobutylmethyl xanthine;
1,3-di-cyclopentylmethyl xanthine;
1,3-di-cyclohexylmethyl xanthine;
1,3-di-cyclopropylmethyl-7-(2-oxopropyl)-xanthine
1,3-di-cyclobutylmethyl-7-(2-oxopropyl)-xanthine;
1,3-di-cyclopentylmethyl-7-(2-oxopropyl)-xanthine;
1,3-di-cyclohexylmethyl-7-(2-oxopropyl)-xanthine;
1,3-di-cyclopentylmethyl-7-(2-hydroxypropyl)-xanthine;
1,3-di-cyclobutylmethyl-7-(2-hydroxypropyl-xanthine;
1,3-di-cyclopropylmethyl-7-n-propyl xanthine;
1,3-di-cyclobutylmethyl-7-n-propyl xanthine; and
1,3,7-tri-cyclopropylmethyl-xanthine; or a pharmaceutically acceptable salt thereof.

10. A compound according to claim 1, being 1,3-di-cyclopropylmethyl xanthine, or a pharmaceutically acceptable salt thereof.

11. A compound according to claim 1, being 1,3-di-cyclopropylmethyl-7-(2-oxopropyl)-xanthine, or a pharmaceutically acceptable salt thereof.

12. A pharmaceutical composition comprising a non-toxic amount of a compound of formula (I) according to claim 1, or where appropriate a pharmaceutically acceptable salt thereof, and a pharmaceutically acceptable carrier.

* * * * *